United States Patent [19]

Rosner et al.

[11] Patent Number: 5,514,552
[45] Date of Patent: May 7, 1996

[54] HYBRID NEURONAL CELL LINES COMPOSITIONS AND METHODS

[75] Inventors: Marsha R. Rosner; Eva M. Eves, both of Chicago, Ill.; Bruce H. Wainer, Chappaqua, N.Y.

[73] Assignee: Arch Development Corporation, Chicago, Ill.

[21] Appl. No.: 56,844

[22] Filed: Apr. 30, 1993

[51] Int. Cl.$^6$ .................. G01N 33/53; C12N 5/16
[52] U.S. Cl. .................. 435/7.21; 435/172.2; 435/172.3; 435/240.26
[58] Field of Search ............ 435/7.21, 172.1, 435/172.2, 172.3, 240.1, 320.1, 7.1, 7.2, 240.26; 436/507

[56] References Cited

PUBLICATIONS

Eves et al. Soc. Neurosci. Abstracts 19:243 (1993).
Lee et al. Exptl Cell Res. 52:219–228 (1990).
Lendahl et al. TNJ 13:131–137 (1990).
Chol et al, Brain Res. 552:67–76 (1991).
Eves et al. Soc. Neurosci. Abs. 16:1149:(Abs. 475.2)(1990).
Jat et al. Mol. Cell Biol. 9:1672–1681 (1989).
Banker, G. and Goslin, K., In *Culturing nerve cells* (ed. G. Banker and K. Goslin), pp. 11–39. MIT Press, Cambridge, Massachusetts, 1991.
Birren, S. J. and Anderson, D. J., a v–myc– Immortalized Sympathoadrenal Progenitor Cell Line in Which Neuronal Differentiation Is Initiated by FGF but Not NGF, *Neuron*, 4:189–201, 1990.
Bottenstein, J. E., Differentiated Properties of Neuronal Cell Lines, In *Functionally differentiated cell lines*, (ed. G. Sato), pp. 155–184, Alan R. Liss, New York, 1981.
Eves, et al, Induction of Rapid Differentiation in Immortalized Rat Septal Cell Lines, *Soc. Neurosci. Abstract*, 17, 37, #21.5, 1991.
Eves, et al, Immortal Cell Lines From Embryonic Rat Hippocampal Precursor Cells, *Soc. Neurosci. Abstract*, 16, 1149, #475.2, 1990.
Frederiksen et al, Immortalization of Precursor Cells from the Mammalian CNS, *Neuron*, 1:439–448, 1988.
Giotta et al, Properties of Two Temperature–Sensitive Rous Sarcoma Virus Transformed Cerebellar Cell Lines, *Brain Res.*, 202:445–458, 1980.
Goslin et al, Development of Neuronal Polarity: GAP–43 Distinguishes Axonal from Dendritic Growth Cones, *Nature*, 336:672–674, 1988.
Greene et al, Neuronal properties of hybrid neuroblastoma×sympathetic ganglion cells, *Proc. Natl. Acad. Sci. USA*, 72:(12)4923–4927, 1975.
Hammond et al,. Development and Characterization of clonal cell lines derived from spetal cholinergic neurons, *Brain Res.*, 512:190–200, 1990.
Hammond et al, Development and Characterization of Clonal Cell Lines Derived from Septal Cholinergic Neurons, *Science*, 234:1237–1240, 1986.
Morimoto, B. H. and Koshland, D. E., Jr., Excitatory amino acid uptake and N–methyl–d–aspartate–mediated secretion in a neural cell line, *Proc. Natl. Acad. Sci. USA*, 87:3518–3521, 1990.
Ronnett et al, Human Cortical Neuronal Cell Line: Establishment from a Patient with Unilateral Megalencephaly, *Science*, 248:603–605, 1990.
Schubert, D., In *Developmental Biology of Cultured Nerve, Muscle, and Glia* (ed. D. Schubert), pp. 1–25. John Wiley, New York, 1984.
Tucker et al, Expression of Epidermal Growth Factor Receptor in Immortalized Rat Hippocampal Cell Lines, *Soc. Neurosci. Abstract*, 16, 1149, #475.3, 1990.
Tucker et al, Expression of Epidermal Growth Factor Receptor in Immortalized Rat Hippocampal Cell Lines, *FASEB J.*, 5, A7267, 1991.
Eves, et al., A Novel Hybrid Immortalization Strategy Yields a More Mature Neuronal Phenotype, *Soc. Neurosci. Abstract*, 19, 243, #107.3, 1993.

*Primary Examiner*—Margaret Parr
*Assistant Examiner*—Phillip Gambel
*Attorney, Agent, or Firm*—Arnold, White & Durkee

[57] ABSTRACT

The present invention provides a process of producing an immortalized hybrid neuronal cell comprising the steps of transducing a primary embryonic brain cell from a specific brain region with a temperature-sensitive oncogene to produce a transductant cell, and fusing the transductant cell with a mature primary neuron from the same brain region to produce the hybrid cell. Hybrid cells produced by such a process are also provided.

8 Claims, 1 Drawing Sheet

FIGURE 1

Brain Region - Specific
Progenitor Cells

Retroviral
Transduction

Progenitor
Cell Line

Mutagenesis

HPRT⁻ Progenitor
Cell Line

Brain Region - Specific
Primary Neurons

PEG

Hybrid Cell Line

HYBRID NEURONAL CELL LINES COMPOSITIONS AND METHODS

TECHNICAL FIELD OF THE INVENTION

The present invention relates in general to novel, immortalized hybrid neuronal cells, in particular, to hybrid septal and hippocampal cells and to a process of making such cells.

The government may own rights in the present invention pursuant to grant number ROI NS-25787 (the National Institutes of Health).

BACKGROUND OF THE INVENTION

The nervous system comprises an extensive array of neuronal pathways that control and modulate virtually all bodily functions. This system develops from a simple neuroectoderma tube, and through a series of processes regulating cell division, commitment, migration, and differentiation, forms functional synaptic connections in a highly specific fashion. These processes involve internal cell programs controlling stage-specific gene expression, cell-cell interactions, and chemical signalling. The result is an organ system of remarkable complexity, responsible for the full range of physiological and intellectual behavior of higher organisms. A major challenge to neurobiologists is understanding the specific cellular and molecular interactions that mediate the formation and/or maintenance of functional connections between particular subsets of neurons and their target cells (Purves, 1988). This goal is made exceedingly difficult by the extensive heterogeneity of cell types and connections even within specific brain regions. For these reasons, a variety of primary cell culture techniques have been developed to provide an approach to simplification of the system for experimental purposes.

These techniques are still limited by the cell heterogeneity of specific regions of brain and the difficulty of obtaining sufficient numbers of cells of a specific type for detailed biochemical and molecular biological studies. One approach that has been employed to circumvent these problems has been the utilization of clonal cell lines that exhibit neuronal features (Bottenstein 1981; Schubert 1984; Banker and Goslin 1991). For example, PC12 cells, arising from a rat pheochromocytoma, have been used in a variety of studies to elucidate the response to and the mechanism of action of nerve growth factor (NGF) (Tishler, et al. 1975; Greene, et al. 1991). Although this approach has provided a considerable amount of information, it is limited for the following reasons.

First, these cell lines are derived from spontaneously arising tumors and therefore carry with them the inherently malignant nature of their cells of origin. Although a recent report has described the isolation of a human neural cell line from nonneoplastic tissue (Ronnett, et al. 1990), the frequency of such spontaneous 'immortalization' events from primary neuronal cells is extremely low. Therefore, the possibility of obtaining cell lines of a specific neurochemical type is unlikely. Second, most of the cell lines currently available represent subclones of single tumors, arising most frequently in the peripheral nervous system, i.e. pheochromocytomas and neuroblastomas, and are therefore of limited usefulness for studying specific processes within particular CNS pathways.

Relatively little work has been carried out with respect to the establishment of permanent cell lines from specific brain regions that elaborate or respond to trophic signals which are involved in the establishment and maintenance of the synaptic circuitry of those regions. Two general strategies are available for engineering such cell lines.

The first is the use of retroviral-mediated introduction (transduction) of oncogenes to 'immortalize' primary brain cells. While this approach is useful for studying the properties of progenitor cells, it is of more limited utility as an approach to the study of differentiated cells. Retroviral transduction is only effective with mitotic cells since the retroviral DNA can only be inserted into the host genome during replication. In addition, once a cell is 'immortalized', it tends to remain locked within a particular developmental window, and in fact, this phenomenon has been exploited by immunologists to study the stages of lymphocyte differentiation (Paige, et al. 1989; Alt, et al. 1987). Therefore, while viral gene transduction might yield cell lines for the study of early stages of neuronal development, it is less likely to provide cell lines that express the phenotypic repertoire of mature neurons which are almost invariably post-mitotic.

A second approach has employed somatic cell fusion techniques in which primary brain cells are fused to a neuroblastoma cell line by exposure to polyethylene glycol (Hammond, et al. 1986). The fusion technique allows one to 'immortalize' cell populations that are post-mitotic and therefore more likely to express highly differentiated neuronal phenotypes. While no current 'cell immortalization' strategy is devoid of limitations, the somatic cell fusion technique makes available large numbers of brain-region-specific clonal cells for cellular and molecular studies of specific neural circuits.

The technique of somatic cell fusion has been widely used to study a variety of cellular and genetic questions (Shay, 1982). Perhaps one of most noteworthy applications has been the generation of lymphoid hybridoma cell lines to produce monoclonal antibodies (Kohler and Milstein, 1975). In the nervous system, somatic cell fusion has been applied to the development of several cell lines derived from sympathetic neurons (Greene, et al., 1975) or dorsal root ganglion cells (Platika, et al., 1985). The cell fusion approach has been previously exploited because of its potential for immortalizing central neurons that are post-mitotic and therefore committed to a particular neurochemical phenotype as well as neuroanatomical pathway (Hammond, et al. 1986; Hammond, et al. 1990; Lee, et al. 1990).

BRIEF SUMMARY OF THE INVENTION

In one aspect, the present invention provides a process of preparing a hybrid neuronal cell from a predefined brain region, which process comprises the steps of:

a) transducing a primary embryonic brain cell from the predefined brain region with a temperature-sensitive oncogene to produce a transductant cell; and b) fusing the transductant cell with a mature primary neuron from that same brain region to produce the hybrid cell.

In a preferred embodiment, the predefined brain region is the septum or the hippocampus. Preferably, the temperature-sensitive oncogene is contained in a retrovirus. In one embodiment, the temperature-sensitive oncogene is a temperature-sensitive mutant of the SV40 large T antigen In another preferred embodiment, a process of the present invention further comprises the step of selecting for the transductant cell before the fusing step. Preferably, selecting is mutagenizing the transductant cell to eliminate the HPRT gene and produce a HPRT⁻ cell, which can be selected against with HAT medium.

In another aspect, the present invention provides a hybrid neuronal cell produced by a process of the present invention.

In a particular embodiment, the present invention provides a process of preparing a hybrid septal cell, which process comprises the steps of:
a) transducing a primary embryonic septal cell with a retrovirus comprising a temperature-sensitive oncogene to produce a transductant cell;
b) mutagenizing the transductant cell to eliminate the HPRT gene and produce a HPRT⁻ cell; and
c) fusing the HPRT⁻ cell with a mature primary septal cell.

In another particular embodiment, the present invention provides a process of preparing a hybrid hippocampal cell, which process comprises the steps of:
a) transducing a primary embryonic hippocampal cell with a retrovirus comprising a temperature-sensitive oncogene to produce a transductant cell;
b) mutagenizing the transductant cell to eliminate the HPRT gene and produce a HPRT⁻ cell; and
c) fusing the HPRT⁻ cell with a mature primary hippocampal cell.

In another aspect, the present invention provides a process of screening a substance for its ability to modulate the function of a neuronal cell from a specific brain region, which process comprises the steps of:
a) providing a hybrid neuronal cell prepared in accordance with the process of set forth above from that specific brain region; and
b) testing the ability of the substance to modulate the function of the hybrid cell.

It is possible to establish progenitor cell lines from specific brain regions using retroviral transduction. The ability to engineer expression of a particular oncogene in a primary cell allows for the potential of greater control over the growth characteristics of the resulting cell line. For example, the use of the temperature-sensitive mutant of the immortalizing SV40 large T antigen provides a potentially precise handle on cell division (Lendahl, et al. 1990; Cepko, 1989). This antigen is stable at 33° C. and promotes cell division. At 37°–39° C. the antigen is inactive and cells are no longer stimulated to divide. Using a retroviral construct containing this gene, a series of progenitor cell lines from a particular predefined brain region of interest (Eves, et al. 1990, 1991; Tucker, et al. 1990, 1991) can be developed and characterized. Such cells likely conserve the lineage features that are unique to the brain region from which they are derived.

It is possible to select and mutate a particular progenitor cell line of interest so that it can be selected against in culture. The HPRT gene is particularly advantageous because it is X-linked and therefore requires only one mutational event. Chemical mutagenesis using agents such as ethane methyl sulfonate are quite efficient in generating HPRT-deficient (HPRT⁻) mutants. The resultant HPRT-deficient cell line is then employed as a fusion partner for primary cells from the same brain region, but at a later stage of development. This approach eliminates the use of the neuroblastoma, provides a growth promoting gene that is better defined and more amenable to control, and allows for the preservation of region-associated cell lineage. The resulting hybrid cell lines express more highly differentiated phenotypes because of the potential of fusing the progenitor line to more mature primary neurons.

BRIEF DESCRIPTION OF THE DRAWINGS

FIG. 1. Schematic illustration of transduction/fusion strategy for generating CNS hybrid cell lines by a process of this invention. Embryonic brain cells (black=short processes) are infected with retroviruses containing an 'immortalizing' oncogene resulting in a 'progenitor' cell line (stippled). The progenitor cell line is subjected to chemical mutagenesis so that the HPRT gene is functionally eliminated. The HPRT⁻ progenitor cell line is then fused to mature primary neurons (black=long processes) from the same brain region, resulting in a hybrid cell line (cross-hatched) that is amenable to growth control, because of the oncogene transduction technique, and which preserves lineage features inherent in the brain region of interest.

DETAILED DESCRIPTION OF THE INVENTION

Figure 1:
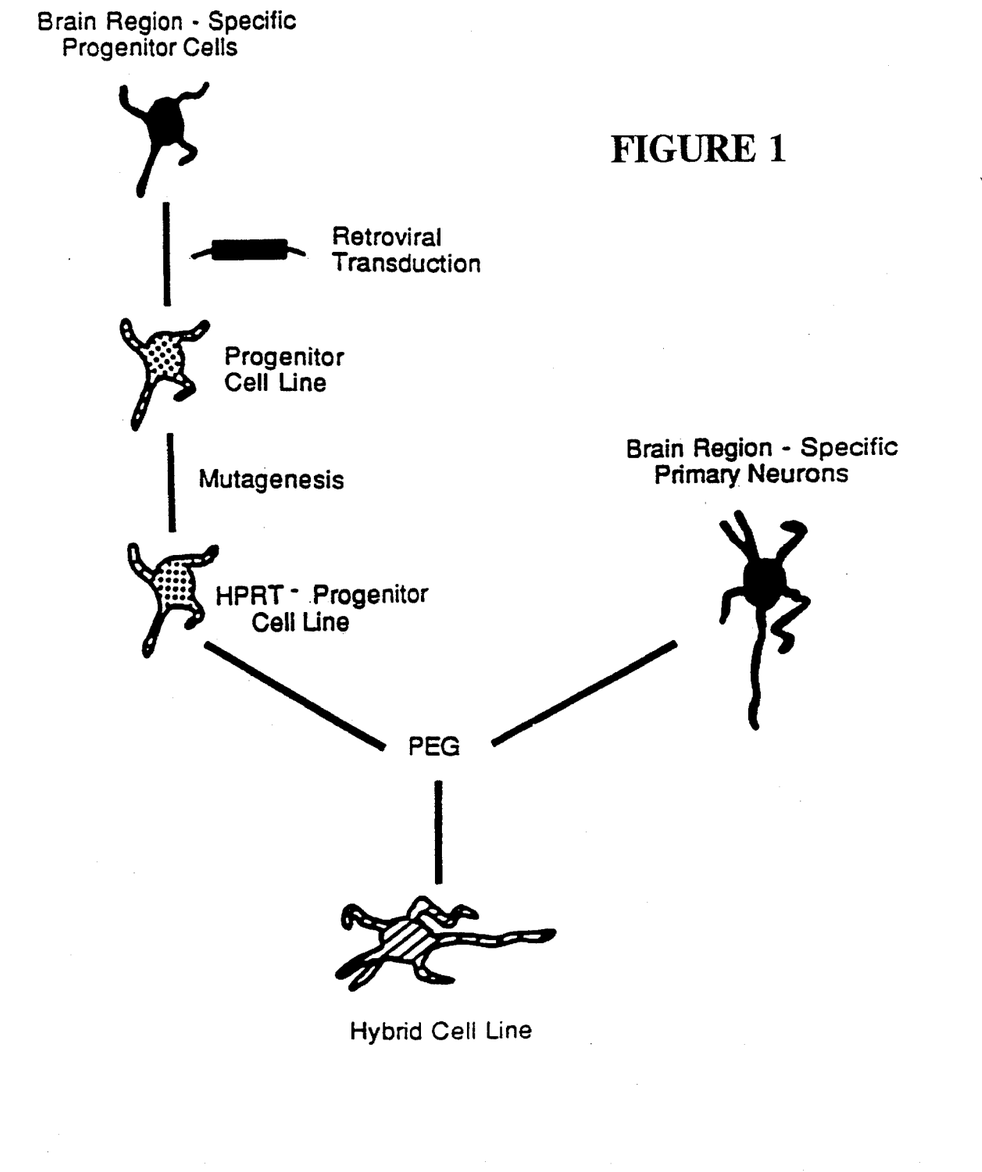

The present invention employs fusion partners of brain cell lineages that have been immortalized via retroviral gene transduction and are already partially differentiated. A preferred oncogene is the temperature-sensitive SV40 large T antigen. The temperature sensitive nature of the SV40 large T antigen insures that the cell lines generated are amenable to control with respect to their growth properties. The retrovirally immortalized neural progenitor cells are employed as fusion partners with mature neuronal cells from the same brain region. Employing fusion partners and differentiated neurons from close or identical lineages increases the likelihood that the resulting hybrid cell lines express a differentiated neuronal phenotype typical of that particular lineage.

Cells from any brain region can be used. In one embodiment, cells from the septal and hippocampal regions are preferred. A brain from any mammal can be used as the source of cells. The dissection, culturing and transducing procedures employed are maximized for each particular cell source.

The only limitation with regard to dissection and isolation conditions of the primary embryonic cell is that the embryonic cell be obtained prior to its "birth date" so that the embryonic cell divides at least once in culture. The "birth dates" of cells from virtually all brain regions are well known by those of skill in the art.

With regard to transducing the embryonic cell, the only limitation is that culture conditions for a particular cell type are such that cell viability of the transductant cell is maintained until the temperature-sensitive oncogene (e.g., T antigen) has exerted its effect. Means for determining appropriate such culture conditions are well known in the art.

Timed pregnancy female rats are chosen in such a way that the transductant parent cells and the primary neuronal parent cells express electrophoretically distinguishable isozymes at three loci, glyoxylase-1 (glo-1, E.C.4.4.1.5), peptidase-3 (pep-1, E.C. 3.4.11), and 6-phosphogluconate dehydrogenase (pgd, E.C.1.1.1.44) (Siciliano, et al. 1987; Bender, et al. 1984). Glo-1 and pgd are on different chromosomes and pep-3, while not yet assigned to a specific chromosome, is not linked to glo-1 (O'Brient 1987). There are also a number of potentially useful differences in isozyme types for the esterase loci (Hedrich 1990). Strain combinations include; ACI and OM or WKY, and WF and OM or WKY (Bender, et al. 1984).

Unless otherwise noted, all cells are maintained in DMEM containing penicillin and streptomycin and 10% fetal bovine serum (FBS)(DMEM-complete). The two plasmids used, pZipSVtsA58 and pZipSVU19tsa, each contain both a temperature sensitive SV40 large T antigen and the neo gene which confers resistance to the antibiotic G418.

These plasmids were transfected into the Ψ-2 NIH 3T3 murine line (Mann, et al. 1983) and the resulting stable producer lines have been provided by P. Jat (Jat, et al. 1986, 1989). The plasmids differ only in that they contain different temperature-sensitive mutants of the SV40 T antigen The plasmids were constructed from the Moloney murine leukemia virus and retain its long terminal repeats with all sequences required for reverse transcription, integration into host DNA, transcription, and transcript processing. The tsSV40 T antigen and neo genes and sequences required for replication in prokaryotic and eukaryotic hosts have replaced viral genes required for encapsidation (Cepko, et at. 1984). The Ψ-2 cells were engineered to provide the encapsidation functions in trans and the virus from the producer lines are capable of only one round of infection (Mann, et al. 1983). The supernatants from these producer lines have viral titres of $5 \times 10^3$ to $4 \times 10^4$/ml as determined by the production of G418 resistant (G418r) clones in populations of naive NIH 3T3 cells.

By way of example, to enhance the likelihood of immortalizing mature septal and hippocampal neurons from rat brain, primary septal and hippocampal cells are placed in a culture environment, first described by Banker and coworkers, that eliminates glial elements in the neuronal plane and results in the growth and differentiation of neurons that have the morphological, neurochemical, and electrophysiological properties of septal or hippocampal neurons (Goslin, et al. 1991). To successfully isolate hybrid cells, it is necessary to eliminate cells from the proliferative parent that are not fused to the primary cells. This is achieved by treating the proliferative parent with chemical mutagens to isolate variant cell lines that are HPRT⁻. Hybrid cells are then selected for in HAT medium (Littlefield 1966). Both the transductant and the hybrid cell lines are examined for expression of neuronal vs glial cytoskeletal features, and neurotransmitter-related markers appropriate to a particular neuronal lineage.

Retroviral transduction of immortalizing genes has produced cell lines capable of neuronal differentiation from CNS cells (Frederiksen, et al. 1988; Giotta, et al. 1980) and PNS cells (Birren, et al. 1990). The degree of neuronal differentiation and the proportion of cells that can be induced to differentiate vary among cell lines and depend on the differentiating regimen employed. No septal lines and only two hippocampal lines immortalized by retroviral transduction have been reported previously. One hippocampal line (Refranz, et al. 1991) does not express neuronal- or glial-specific markers in culture but appears to take on mature neuronal and glial morphologies when transplanted into either the hippocampus or cerebellum of neonatal rats.

Using retroviral transduction of two different temperature-sensitive (ts) SV40 large T-antigens, 16 cell lines have been isolated from embryonic day 17 (E17) rat hippocampal cells, 7 lines from E18 rat hippocampal cells and 5 lines from E17 rat septal cells. Infection of E13 rat septal cells produced no surviving colonies; the cells that survived infection aggregated to form hollow spheres that failed to adhere to the substrate and disintegrated over a 10 day period. A first attempt of transduction of E15 septal cells produced only three clones. Hypothesizing that the septal cells were not surviving the interim between plating and full expression of the ts T antigen, we altered the conditions of infection and early culture and have isolated 29 lines from E15 septal cells.

The initial observations on morphological differentiation and response to NGF in the recently obtained septal transductants suggest that the altered protocol used to produce the septal transductants may be superior to our original protocol. The septa is dissected from E14–15 and the hippocampi from E16–18 rat embryos when the target cells are undergoing their final divisions (Bayer 1979, 1980). The cells are dissociated with trypsin and mechanical shearing and plated onto polylysine (15 μg/ml) coated tissue culture dishes. The cells are plated in 6-well dishes and infected immediately after plating. Two hours after the initiation of infection additional DMEM-complete is added and coverslips carrying primary glia, pretreated for two days with the antimitotic cytosine arabinoside, are inverted over the infected cells. G418 (250 μg/ml) is added 48 hrs later. G418r clones are isolated and expanded at 33° C.

Two $\phi_2$ NIH 3T3 lines that produce replication-defective retrovirus carrying the neo gene (producing resistance to G418) and either the tsA58 or the U19tsa temperature-sensitive mutation of the simian virus 40 large tumor antigen gene were obtained from P. Jat (Ludwig Institute for Cancer Research) (Jat et al., 1989). The mutant large tumor antigens are functional at 33° C. and defective at 37°–39° C.

Hippocampi were dissected from embryonic day 17 (E17) Holtzman and E18 Wistar-Kyoto rat embryos. Cells were dissociated with 0.25% trypsin and plated in DMEM-complete (Dulbecco's modified Eagle medium/10% fetal bovine serum (FBS)/2 mM L-glutamine/penicillin at 50 units/ml/ streptomycin at 50 μg/ml) in tissue-culture dishes coated with polyornithine (15 μg/ml). Retroviral infection was done the following day as previously described (Jat et al., 1989), except that the cells were not subcultured before selection with G418 at 250 μg/ml. Single clones were isolated 2–4 weeks after infection.

Screening for Differentiation

One day after plating in DMEM-complete at 33° C., the culture medium was replaced with low-serum (1% FBS) DMEM containing 20 nM hydrocortisone, 0.3 nM triiodothyronine, 0.1 mM putrescine, 20 nM progesterone, 1 pM estradiol, 30 nM $NaSeO_3$, transferrin at 1 μg/ml, and insulin at 5 μg/ml (IsDMEM), and the cultures were shifted to 39° C. (nonpermissive temperature). When used, the differentiation agent 10 nM phorbol 12,13-dibutyrate ($PBt_2$) was added on day 3. Growth arrest and morphological changes were microscopically assessed on day 6 or 7.

The lines were evaluated for changes in growth rate upon a shift from 33° C. to 39° C. Twenty of 22 lines slowed division at 39° C., reflecting expression of the ts large tumor antigens. Cell lines that did not display any obvious reduction in growth rate at 39° C. were not included in further characterization studies. For cell lines of particular interest, conditional proliferation was confirmed by [³H]thymidine incorporation studies. After differentiation, the lines tested had 10-fold or greater reductions in the amount of [³H] thymidine incorporated compared with undifferentiated cultures. When 10% FBS was added to differentiated cells and the cultures were maintained at 39° C., the cells reacquired the flat, spreading morphology of cells at 39° C. in high serum but did not incorporate [³H]thymidine, indicating that differentiated cells were viable and plastic with respect to morphology but were not returned to proliferation by the mitogenic factors in FBS.

Twenty-two of 28 hippocampal lines exhibited this response to XAN; in 14 lines an estimated 50% or more of the cells differentiated. Two XAN-inducible lines were used to analyze the effects of the XAN components with respect to induction and survival. X or A alone produced essentially the same effect on morphology as XAN. However, with A alone more cells survived and the survivors gradually returned to the pre-treatment morphology. XA treatment was as effective and as lethal as XAN treatment. Although NGF alone had no discernable effect on morphology, it had two more subtle effects; in combination with A the cells developed more complex processes early (1 hr) in the course of differentiation than were seen with A alone, and NX and NA treated cultures displayed somewhat better survival than X or A treated cultures. These small effects suggested that the cells might have functional NGF receptors (NGFR). Immunocytochemical analysis revealed that a subset of the differentiated cells were positive for LNGFR. Immunocytochemical staining with trk antibodies also revealed a subset of positive cells in two lines, AS 19-3 and AS583-6. The latter exhibits a more homogeneous morphological response to treatment and higher viability post-treatment. Post-treatment viability was improved by treating with 10 μM forskolin, an agent that like isobutyl methylxanthine and dibutyryl cAMP acts to increase intracellular cAMP levels. Forskolin is now used routinely to differentiate these cells. Preliminary immunocytochemical analysis indicates that lines that differentiate are NFP+ GFAP−. No GFAP+ lines have as yet been identified.

H19-7, an NFP+ GFAP− line, which exhibits induction for morphological and biochemical differentiation and has a diploid chromosome complement was chosen to derive HPRT− mutants to serve as the immortal parent(s) in somatic-cell hybridization. Nineteen TG-resistant mutants isolated from 10 independent cultures were characterized for sensitivity to HAT, growth arrest and morphological differentiation at 39° C., and, for selected mutants, NFP and MAP2 expression following differentiation. H19-7TG53 was chosen as the best fusion partner candidate and an initial fusion was performed with P21 rat hippocampal cells. 72 HAT-resistant colonies were isolated.

Method Of Determining Growth Rate at Non-Permissive Temperatures

Cells were placed at about 104 cells per well in polyllysine-coated 12-well culture plates. Parallel wells were either maintained at 33° C. in DMEM-complete or subjected to the differentiation protocol described above. Then the medium was replaced with fresh IsDMEM containing [$^3$H] thymidine at 2 μCi/ml (1 Ci=GBq) for 24 hr. The cells were then fixed in cold 5 % (vol/vol) trichloroacetic acid for 20 rain and washed with 100% ethanol. The acid-insoluble precipitate was solubilized with 400 μl of 0.1 M NaOH for 30 rain at 65° C., neutralized with 27 μl of $H_3PO_4$, and added to 8 ml of scintillation fluid.

Neural differentiation in the hippocampal lines was first evaluated at the level of morphology. Those lines in which some proportion of the cells elaborated processes after serum reduction at 39° C., with or without $PBt_2$ addition, are considered capable of differentiation. Several agents including dibutyryl cAMP $PBt_2$, and a mixture (dibutylryl cAMP/ isobutylmethylanthine/NGF) used by Ronnett et al. to induce morphological differentiation in a spontaneous human cortical line (Ronnett et al., 1990) elicited differentiation in these cells. $PBt_2$ was chosen initially as the differentiating agent because it induces morphological differentiation in many of the lines after a single low-dose exposure (10 nM), and less toxicity was observed. Agents that had no evident effect on morphology include sodium butyrate, retinoic acid, and NGF. Those lines in which at least half of the cells differentiated or in which some cells extended very long or elaborate processes were further characterized.

Proliferating and differentiated cultures were stained immunochemically using antibodies to GFAP and NFPs. The proportion of cells that stained positively and the staining intensity varied from line to line. For example, line H19-7 did not stain for NFP before induction; after induction most H19-7 cells stained positively for NFP. In contrast, most WH19-4 cells stained for NFP both before and after induction. The results indicated that cells of neuronal lineage (NFP$^+$ GFAP$^-$) and of glial lineage (NFP$^-$ GFAP$^+$), as well as uncommitted progenitors (NFP$^+$ GFAP$^+$), had been immortalized.

NFP-positive lines were further characterized by using antibodies to MAP-2 and GAP-43. In mature neurons MAP-2 is found predominantly in cell bodies and dendrites, and GAP-43 is found predominantly in cell bodies and axons, whereas in neurons undergoing maturation in culture, both markers are initially distributed throughout the cell. All NFP$^+$ lines also expressed MAP-2. Six of 10 NFP$^+$ MAP 2$^+$ lines expressed GAP-43. A NFP$^{31}$ $^{GFAP+}$ line, H19-1, expressed neither marker. None of the lines tested appeared to exhibit segregation of MAP-2 versus GAP-43 immunoreactivity in a pattern indicative or dendritic and axonal differentiation.

Antibodies recognizing neurofilament protein (NFP) subunits and glial fibrillary acidic protein (GFAP) were from V. Lee (University of Pennsylvania) (Lee, et al., 1984, 1987; Trojanowski, et at, 1989). Antibody to microtubule-associated protein 2 (MAP-2) (Binder et al., 1986) was obtained from L. Binder (University of Alabama). Antibody to the 43-kDa growth-associated phosphoprotein (GAP-43) (Goslin, et al., 1988) was obtained from D. Schreyer (Stanford University). Low-affinity NGF receptor was detected with monoclonal antibody 192 IgG (Chandler, et al., 1984). Choline acetyltransferase was detected with monoclonal antibody AB8 (Levey et al., 1983). Cells were fixed in 3% (wt/vol) paraformaldehyde/0.1% glutaraldehyde in 0.1 M phosphate (pH 7.4), blocked with 5 % (wt/vol) milk in Tris-buffered saline (TBS; 0.05 M Tris/0.14 M NaCl, pH 7.4) (30 min), and incubated at 4° C. with primary (16 hr) and secondary (16 hr) antibodies and peroxidase-antiperoxidase (4 hr). Immunoreactivity was visualized with diaminobenzidine at 0.5 mg/ml/0.01% peroxide in TBS.

RNA isolation, blotting, hybridization, and analysis were done using standard techniques. The probes were a 0.9-kilobase (kb) Pst I fragment of mouse NGF cDNA from L. Reichardt (University of California at San Francisco) (Large, et al., 1986), a 1.1-kb rat BDNF cDNA clone from G. Yancopoulos (Regeneron Pharmaceuticals) (Maisonpierre et al., 1991), and a 1-kb NT-3 PCR fragment from rat genomic DNA Or. Large, Case Western Reserve University).

Bilaminar cultures were set up as described by Banker and Cowan and modified by Scholz and Palfrey (Scholz, et al., 1991). Primary glial layers were from 2-day-old rat cortices and were used directly or passaged once. The neuronal layer was prepared from freshly dissociated cells from specific embryonic brain regions (E16 septa). Two days after plating the neuronal layer, antimitotic (15 μM cytosine β-D-arabinofuranoside) was added to prevent glial overgrowth and progenitor cell proliferation.

Using retroviral transduction of the tsA58 and U19tsa simian virus 40 large tumor antigens, 16 clones from E17 Holtzman and six cell lines from E18 Wistar-Kyoto rat hippocampi were immortalized. In general, at 33° C., the cells were polygonal and quite flat with prominent nuclei when viewed with phase optics. Some of the clones exhibited morphological heterogeneity at 33° C., which persisted after subcloning and may be attributable to the immortalization of multipotential progenitors. Population-doubling times were estimated by counting cells in discrete clones on successive days after plating. For four lines the doubling times ranged from 22 to 31 hr.

Differentiation in these cell lines depended both on the inactivation of the ts large tumor antigen and on environmental conditions. Culture at 39° C. produced an extremely flat cell morphology, but serum reduction was required for distinct process formation. Morphological differentiation after FBS withdrawal has been described for a number of permanent neuronal and glial lines including PC12 cells. In many lines, the effect of reduced serum is potentiated by $PBt_2$ treatment.

Several $NFP^+$ $GFAP^-$ hippocampal lines were responsive to factors secreted by primary glia. H19-7 is a line of particular interest as a good example of a ts neuronal progenitor; upon induction it ceased DNA replication and cell division and exhibited a high degree of morphological differentiation, its expression of neuronal markers was inducible, and it did not express GFAP. When H19-7 was plated onto coverslips and placed at 37° C., in lsDMEM, over a layer of glia treated with an antimitotic, the cells differentiated more rapidly and to a greater extent than when plated alone. However, the H19-7 cells did not attain the morphology or NFP repertoire of primary rat hippocampal neurons undergoing maturation in the same culture system. The limited maturation of the H19-7 cells could be a consequence of progenitor immortalization or of the clonal nature of the line.

Another line of particular interest is H19-5, a $GFAP^+$ $NFP^-$ line. H19-5 cells have been used to substitute for the glial layer in bilaminar cultures where they maintain the viability of and support the normal in vitro differentiation of E16 rat septal neurons. Parallel 7-day cultures of septal neurons over glia or over H19-5 were stained immunochemically for NFP, GAP-43, low-affinity NGF receptor and choline acetyltransferase. No evident differences were detected in viability or the proportions of cells expressing these markers. In contrast, primary septal neurons plated over a mouse fibroblast line, NIH 3T3, die within 4 days. H19-5 cells also support the morphological differentiation of selected neuronal cell lines to the same degree as do primary glia.

Of the 29 E15 septal transductant lines generated employing the transduction protocol, 28 demonstrate reductions in growth rate at the non-permissive temperature. The induction protocol used to differentiate the hippocampal lines (39° C., low serum and phorbol ester) did not produce any evident morphological differentiation in initial screens (9 lines). However, a cocktail of inducing agents (XAN=0.5 mM isobutyl methylxanthine, 0.5 mM dibutyryl cAMP, 25 ng/ml NGF) (Ronnett, et al. 1990) caused many of these lines to undergo rapid morphological alteration changing from a flat epithelioid morphology to cells with small refractile cell bodies and multiple complex processes. This effect was evident by 30 min and reached a maximum by approximately 4 hr. By 24 hr post-induction most of the cells that responded died.

A bilaminar culture system is used to enrich for particular populations of primary neurons. Virtually all cells present on the neuronal plane stain strongly for NFPs, whereas at most a fraction of one percent stains positively for GFAP; the converse is true of the glial plane. Septal cultures were examined neurochemically by immunostaining for ChAT, GABA, and LNGFR, markers which identify primarily septohippo-campal projection neurons (Wainer, et al. 985; Dreyfus, et al. 1989; Springer, et al. 1987; Freund, et al. 1988). Cholinergic and GABAergic neurons constitute approximately 5 % and 38 % of the total cell population, whereas LNGFR-positive cells comprise approximately 15 % of the total.

It should be noted that in other septal culture systems cholinergic neurons are rarely more than 1% of the total population (Hartikka, et al. 1988). When NGF (100 ng/ml) was added to these septal cultures there was no increase in the proportion of ChAT-immunoreactive neurons although ChAT activity was significantly elevated. The addition of anti-NGF antibodies did not alter the number of cholinergic neurons indicating that essential trophic factors, in addition to NGF, are elaborated by the glial cells. Septal neurons die rapidly when transferred from the coculture to glial-conditioned medium. However, preliminary observations indicate that addition of NGF to this medium rescued a subpopulation of the septal neurons. The identity of this subpopulation is under investigation.

Since cholinergic neurons tend to be born relatively early (Semba, et al. 1988; Bayer 1979), it may be possible to further increase their proportion in these culture by utilizing E13–14 animals. The substantial numbers of cholinergic and NGFR-positive neurons obtained in this particular culture system should significantly increase the frequency of hybrid cell generation from neuronal subpopulations of interest in the proposed project. However, the fact that we have generated a large number of lines through fusion of neuroblastoma cells with neurons from young adult brains strongly supports the feasibility of this approach. Young adult neurons are at least as differentiated and probably have formed more intercellular contacts than those grown in the bilaminar cultures.

In addition, the findings that the neurotrophins are mitogenic for fibroblasts expressing their respective receptors (Klein, et al. 1991; Cordon-Cardo, et al. 1991) and possibly neuroprogenitor cells (Cattaneo, et al. 1990) suggests that the inclusion of the neurotrophins in the culture medium following infection might foster mitosis in proliferating cells expressing the receptors. Thus, the neurotrophins could act as selective agents for receptor-positive cells by increasing their relative proliferation rates. Therefore, some of the plates will contain neurotrophins during infection and initial culture of transductants. Clones are assessed for growth cessation at 37° C.–39° C. Maintenance cultures contain G418 to prevent loss of the vector. Neuronal, NGF-responsive transductants have been generated and the degree of morphological differentiation attainable by these lines is greater than we have seen with the hippocampal transductants.

The transductant lines are screened to determine which lines have the most extensive array of mature neuronal phenotypes. The transductant lines are subjected to one of two simple induction protocols. The cells are plated at 33° C. (day 0). On day 1, the cells are shifted to 39° C. and the high serum medium (DMEM-complete) is replaced by lsDMEM (DMEM supplemented with 0.2 nM hydrocortisone, 3.0 pM tri-iodo thyronine, 100 nM putrescine, 0.2 nM progesterone, 0.01 pM estradiol, 10 ng/ml transferrin, 50 ng/ml insulin and 0.3 nM NaSeO3 containing 1% FBS). For hippocampal lines, 10 nM phorbol dibutyrate is added on day 3. The cells are evaluated for growth arrest and morphological differentiation compared to control cultures on day 7. Cells are processed on day 7 or 8 for immunocytochemistry or RNA analysis. For septal lines, 10 µM forskolin is added on day 3 and the cells are evaluated at 4 hr and 24 hr after forskolin addition at which times the cells are processed for immunocytochemistry or RNA analysis. These induction protocols identify lines capable of morphological differentiation, a primary criterion for neural differentiation.

It is possible that other factors will have more profound effects on neurochemical phenotype. Numerous compounds have been demonstrated to have trophic effects on primary neurons or neuronal cell lines. PC12 cells respond at the morphological and biochemical levels to NGF, FGF, butyrate and cAMP analogs (Tishler, et al. 1975; Bay, et al. 1990). Retinoic acid induces NGF-responsiveness in immature chick sympathetic neurons (Rodriquez-Tebar, et al. 1991) and in LA-N-1 cells (Haskell, et al. 1987). bFGF induces NGF-responsiveness in a sympathoadrenal cell line (Birren, et al. 1990). Interleukin-3 has been demonstrated to upregulate ChAT expression in one of our first generation cell lines (Kamegai, et al. 1990).

Transductant lines that demonstrate growth arrest at 39° C. and morphogenesis in response to induction (i.e., formation of refractile processes) are further characterized. Since the transductant lines are generated from embryonic cells, it is possible that they cannot be induced to express the phenotypic repertoire of mature neurons or of some of the previously developed hybrid cell lines. Therefore characterization of transductant cell lines is performed sequentially. For example, in septal transductant lines, initial characterization would include immunocytochemical analyses of NFP and GFAP, and mRNA and immunocytochemical analyses for neurotransmitter markers such as ChAT and GABA, and for the neurotrophin receptors. If a cell line stains positively for NFP and negatively for GFAP, the other cytoskeletal markers are evaluated such as MAP2, GAP43, and synapsin I. If any neurotransmitter markers are positive, a more complete evaluation includes measurement of transmitter enzyme (i.e., ChAT or GAD) activities, uptake and release studies. A similar strategy is applied to the characterization of the hippocampal transductant cell lines, except that the focus is on excitatory amino acid transmitters, neurotrophin expression, and trkB and EGFR expression. Subcloning is employed to enhance the expression of desired characteristics in lines with great cell-m-cell variation. Analysis of marker mRNA expression in the subclones employs RNA dot-blots to increase the efficiency of screening.

Characterization of Septal and Hippocampal Hybrids

A variety of antibodies recognize proteins characteristic of neurons (e.g., NFP, MAP2, GAP43, synapsin I) and non-neuronal cells (e.g., GFAP, cytokeratins). The cell-specific nature of these reagents has been previously established (Lee, et al. 1987; Tucker, et al. 1988; Goslin, et al. 1988; Lee, et al. 1984). Transductant lines found to be responsive to temperature and chemical agents are examined for their capacity to express these markers. Initial screening is performed by immunocytochemical detection of these markers under normal and differentiating culture conditions. Lines which stain for markers of interest are re-examined by immunoblot to confirm the staining results. These lines are then examined for their neurotransmitter and excitable properties.

The excitable properties of any cell lines of interest are evaluated. Such properties include the evaluation of ionic conductances sufficient for the generation of an action potential, conductances selectively observed in septal or hippocampal neurons, as well as the response of cell lines to cholinergic, GABAergic, and excitatory amino acid agonists and antagonists.

The transductant and hybrid lines are evaluated for their expression of NGF, BDNF, NT-3, LNGFR, trk, trkB, trkC and NT-4 (Hallbook, et al. 1991). Initial screenings of hippocampal transductants have revealed cell-line intrinsic patterns of NGF, BDNF, and NT-3 mRNA expression and changes in their expression patterns with differentiation. Screening of septal transductants has demonstrated lines that are immunoreactive for LNGFR and trk. Findings indicate that at least one of these lines, AS583-6, is NGF-responsive. Gene expression analyses employ RNA blot methodologies. Total RNA is isolated from cultures using a guanidinium isothiocyanate method (Chomczynski 1987). 25 µg of total RNA per lane are electrophoresed through a 1.2 % agarose/1.1% formaldehyde gel (Ausubel, et al. 1989) and capillary blotted onto GeneScreen (Roback, et al. 1990; Large, et al. 1986). Appropriate tissue standards are co-electrophoresed to facilitate gel to gel comparison. The membrane is exposed to UV light to covalently cross-link RNA. Probe synthesis, hybridization, and washing parameters are as follows. Membranes are first pre-hybridized at 50° C. for 24 hours in 50% formamide, 5 % SDS, 5× Denhardts, 5×standard saline-phosphate-EDTA (SSPE), and 200 µg/ml salmon sperm (SS) DNA. The probes are as follows: 0.9kb fragment of the mouse NGF eDNA (Dr. Louis Reichardt, UCSF (Shelton, et al. 1984)); 1.1 kb fragment of rat BDNF eDNA (G. Yancopoulos, Regeneron) (Maisonpierre, et al. 1991); 1.0 kb NT-3 PCR fragment from rat genomic DNA (T. Large, Case Western. Reserve Univ.); 1.0 kb fragment of rat LNGFR cDNA (Dr. Eric Shooter, Stanford University (Radeke, et al. 1987)); 201bp fragment of mouse trk eDNA, 3.2 kb fragment of mouse trkB eDNA, and 570bp mouse trkC eDNA (M. Barbacid, Bristol-Myers Squibb (Lamballe, et al. 1991; Martin-Zanca, et al. 1990; Klein, et al. 1989)).

In each case, these probes are either in M13 or pBlueScript. Single-stranded phage DNA is isolated, the appropriate primer is annealed and extended with the Klenow fragment of DNA polymerase I in the presence of 32P-dCTP. The labeled probe is separated from the vector on an alkaline agarose gel (Maniatis, et al. 1987), and then added to the hybridization buffer consisting of 50% formamide, 5 % SDS, 1X Denhardts, and 200 µg/ml SS (salmon-sperm) DNA. The prehybridized membrane is incubated in the hybridization buffer at 50 µC for 24 hours. The membrane is washed in 1X standard saline-citrate (SSC)/0.1% SDS at room temperature for 30 minutes followed by 0.1×SSC/0.1% SDS at room temperature for 30 minutes, and then 2 washes at between 60° C.–65° C. (depending on probe) for 15 minutes each in 0.1×SSC/0.1% SDS. The membrane is exposed to X-ray film (Kodak XAR-5) and the intensity of the specific bands on the resulting autoradiogram is quantified using a scanning laser densitometer. The signal for each band is then normalized to total mRNA per lane determined by reprobing the membrane with a 5'− end-labelled poly(dT)18 probe under conditions essentially as describe above except that hybridization is at 37° C. and all washes are performed at room temperature. Immunological agents for quantitative analysis of neurotrophin protein expression are at present only available for NGF protein, for which a 2-site ELISA specific for βINGF (Weskamp, et al. 1987) has been regularly employed ( Lee, et al. 1990; Roback, et al. 1990).

Crude cell lysates from cultures are applied to microtiter plates coated with goat anti-βNGF. Bound NGF is visualized by serially incubating the wells with monoclonal antibody to β-NGF, biotinylated goat anti-rat IgG, horseradish peroxidase conjugated to streptavidin, and orthophenylenediamine. Absorbance values of the samples are compared to values obtained from known quantities of purified male mouse submaxillary β-NGF. Background signal is obtained by coating wells with pre-immune goat serum rather than the anti-NGF serum. Total protein concentration of each sample is determined by the method of Bradford (Bradford, 1976). The NGF ELISA has a sensitivity of 0.1–1 pg of NGF per assay, and recovery of NGF from the samples is routinely 90–100%.

Septal Cells

Most septal neurons which project to the hippocampus utilize ACh or GABA as their neurotransmitter. To screen for the cholinergic phenotype, immunocytochemical and radiochemical assays specific for ChAT are performed on the septal lines (Levey, et al. 1983; Fonnum 1975). The lines found to express the highest levels of ChAT are further evaluated for the following components of ACh turnover: i) high-affinity sodium-dependent choline uptake and ACh synthesis; and ii) ACh release following depolarization with high K+ (Richardson, et al. 1989). ChAT mRNA expression is quantified with RNA blots employing a cDNA probe (provided by Dr. Ibenez at the Karolinska Institute). The septal lines are also screened for GABA and GAD mRNAs. GAD mRNA expression is quantified with RNA blots employing a eDNA probe (provided by Dr. Gottlieb at the Washington University, St. Louis). Techniques for extracting RNA and general RNA blotting procedures are well known.

Lines expressing GAD mRNA are assayed for GAD immunoreactivity and enzymatic activity by incubating cell homogenates with L-[1-14C]glutamic acid, and then measuring 14CO2 released from labeled GABA (Gottlieb, et al. 1988). Lines which exhibit high levels of GAD activity are evaluated for GABA content via HPLC (Kontur, et al. 1984), and for [3H]-GABA uptake and release (Shalaby, et al. 1987).

Hippocampal Cells

Hippocampal pyramidal neurons are neurochemically characterized by their expression of high levels of excitatory amino acids such as glutamate and aspartate as well as high affinity uptake and release mechanisms for these substances (Cotman, et al. 1987).

Although a neuroblastoma line has been reported to exhibit properties suggestive of the presence of NMDA receptors (Morimoto, et al. 1990), there are currently no cell lines that express definitively characterized NMDA receptors. As an initial screen, hippocampal cell lines are tested for an increase in Ca++ influx following glutamate treatment using an microspectrofluorometric image analysis system. This system takes advantage of the fluorescence emitted by the Ca ++ ionophore Fura-2 when bound to free Ca++. This rapid procedure allows efficient identification of any lines expressing functional glutamate receptors. A permanent cell line expressing the NMDA receptor would facilitate further evaluation of the biochemical and functional properties of such receptors as well as providing a ready screening system for both putative agonists and antagonists. Since cholinoceptive hippocampal neurons express muscarinic receptors, the hippocampal lines are screened for the presence of M1 muscarinic binding behaviors. Lines which exhibit binding are further evaluated for muscarinic subtype-specific mRNA species.

A combination of clonal cell lines and bilaminar culture is used to determine whether trophic effects are specific to primary hippocampal cells by using primary cerebellar cells as a control. Each septal line is cocultured with primary hippocampal cells, both neurons and glia. The clonal lines are cultured on coverslips and the hippocampal cells are plated on the bottom of the wells; thus, since the septal and hippocampal cells are not in direct contact, any trophic interactions are likely mediated by diffusible factors. At 7, 10 and 15 days after establishing cultures, the septal plane is analyzed for ChAT, GABA, LNGFR, NFP, and trk family immunoreactivity. Some coverslips are also analyzed for cell survival using the vital dyes fluorescein diacetate and propidium iodide (Favaron, et al. 1988). In addition, some coverslips are used for neurochemical analysis of ChAT and/or GAD activities. Although the eventual isolation of a trophic factor is most expeditious if it is a diffusible molecule, it is possible that membrane-bound molecules also exert trophic support. For this reason, studies are repeated by coculturing the septal lines and the primary hippocampal cells in a standard monolayer culture paradigm at a high enough density to allow substantial cell-cell contact.

Hippocampal lines are cocultured with primary septal neurons both in bilaminar cultures (with the septal neurons on coverslips) and together on a single plane as described above. The response of primary septal neurons to the hippocampal cells is analyzed as above. To assay for synaptogenesis, cocultures of cell lines carrying a β-galactosidase construct and primary neurons on a coverslip are established using a standard bilaminar approach with supporting glia. These cultures are at a low enough density to permit ultrastructural assessment of synapse formation. The β-galactosidase reaction product allows identification of immortalized cells at both the light microscope and ultrastructural level. In preliminary studies with the previously generated hybrid cell lines, synaptic structures have been seen.

The transductant or hybrid cells are labeled with rhodamine-conjugated latex spheres. The spheres label the entire cell and permit fluorescent and electron microscopic identification of tagged cells for over three weeks in vitro. The cultures are monitored under the light microscope for evidence of process formation and under fluorescence to assess cell-cell interactions. At appropriate times the cultures are evaluated for electrophysiological and ultrastructural evidence of synapse formation. Some cultures are immunocytochemically stained for GAP43, MAP2, synapsin I, and highly phosphorylated NFP isoforms to examine selective channeling of proteins into putative dendrites and axons. In the second step of our screening strategy each of the "active" hippocampal lines is cocultured with each of the "responsive" septal lines. The same endpoints are used as above.

Antibody-mediated neutralization is the most straightforward approach to determining whether previously-defined trophic factors constitute the active protein(s) released by cell lines of interest. For many trophic and growth factors such as NGF, FGF and EGF, neutralizing antibodies are available. For those factors for which neutralizing antibodies are not available (e.g., currently BDNF and NT-3) antisense RNA methods are employed. Two approaches to antisense RNA-mediated mRNA neutralization are the use of synthetic oligonucleotides (Zon 1988; Caceres, et al. 1990) and expression plasmids (Katsuki, et al. 1988). The second approach is preferred because 1) synthetic oligonucleotides likely on all cells in culture whereas plasmids are likely specific for the transfected cells they occupy; 2) extremely large quantities of expensive synthetic oligonucleotides are required for the antisense studies; and 3) the effects of antisense expression can more easily be assessed with the plasmid constructs since transfectants can be grown in bulk culture and antisense effectiveness can be determined prior to co-culture with primary neurons.

However, in cell lines that synthesize multiple neurotrophic factors it may be necessary to neutralize all of the factors. In this case, synthetic oligonucleotides are the better choice since it may be difficult to create transfectant cell lines containing all of the necessary antisense expression constructs. Neutralizing antibodies and antisense methodologies can certainly be used in conjunction.

Antisense expression constructs (and sense constructs to serve as controls) are prepared in the inducible expression vector pMSG (Pharmacia (Lee, et al. 1981)) which has the selectable marker gpt (bacterial xanthine-guanine phosphoribosyl transferase). Restriction enzyme digestion of the NGF, BDNF, and NT-3 cDNA clones described above release fragments unique to each neurotrophin. These fragments are then subcloned into pMSG using standard methods (Sambrook, et al. 1989), and both sense and antisense constructs for each neurotrophin are identified by restriction enzyme digestion and confirmed by sequencing. The constructs are then transfected into the selected transductant line(s) (Sambrook, et al. 1989), stable gpt-expressing transfectants selected by culturing in media containing aminopterin, mycophenolic acid, hypoxanthine, xanthine, and thymidine (Mulligan, et al. 1981), and then antisense activity determined using RNA blotting (with both sense and antisense probes). In addition, ELISA or immunoblot assays will be performed where possible to confirm that production of the protein is eliminated or greatly reduced.

Transfectants are then used in the previous culture paradigms to determine what effect antisense expression had on the previously-observed trophic effects, employing cells transfected with the appropriate sense constructs as controls.

Transductant Characterization

In potentially useful transductant cell lines, karyotype analyses are performed to eliminate lines or subclones that are aneuploid or exhibit gross chromosomal abnormalities. Similar analyses have been performed for the previously characterized hybrid cell lines (Hammond, et al. 1986, 1990; Lee, et at. 1990). H19-7, the hippocampal transductant line chosen for mutagenesis and fusion has a diploid chromosome complement. Chromosome preparations and banding are done basically as described (Eves, et al. 1981) except that longer incubations in colchicine will be required due to the longer cycling time of the transductants (A 16 hr colchicine incubation was found to be sufficient for H19-7). In cell lines with normal karyotypes, isozyme analyses are performed for the markers described above. For transductant lines from random-bred rats, this analysis identifies an appropriate strain of inbred rat to be employed as the source of primary cells for fusion studies.

To obtain HPRT-deficient mutants in selected transductant cell lines via chemical mutagenesis. Transductant lines selected by the criteria above are treated with ethyl methanesulfonic acid (EMS) to obtain mutants deficient in hypoxanthine phosphoribosyltransferase activity (HPRT−). This normally dispensable activity is selected against with 6-thioguanine (6TG) and selected for with aminopterin in the presence of hypoxanthine and thymidine (HAT). Since the HPRT gene is on the X chromosome, the production of a mutant requires only a single hit. Plating efficiencies and EMS-toxicity curves are determined and transductant cells are treated with EMS at concentrations sufficient to kill 50% of the cells. This level of survival has produced adequate numbers of mutants in other systems (Eves, et al. 1981; Hsie, et al. 1975; O'Neill, et al. 1977; Shaw, et al. 1978; Eves, et al. 1983). The typical concentration range of EMS for mutagenesis of diploid immortalized cell lines is 100–1000 µg/ml. EMS treatment time is equal to about 1–1.5 times the cell doubling time. Following EMS treatment, the cells are subcultured every 2 days for 7 days to allow for expression of the mutation, and then HPRT− mutants are selected by the addition of 6TG to the medium. Mutants are tested for frequency of reversion in HAT medium (a reversion frequency of less than $10^{-7}$/cell is acceptable). H19-7 has a doubling-time of 22 hours and a plating efficiency of 90%. 100 µg/ml EMS for 30 hr was sufficient to kill 50% of the cells.

The bilaminar culture system for primary CNS cells, originally developed by Banker and coworkers (Goslin, et al. 1991; Banker, et al. 1979), is used for rat primary septal and hippocampal cultures. Glial cultures are established from rat neocortical cells of postnatal age 2 days. Brains are removed from the rat pups aseptically, bisected down the midline, and the brainstem and thalamus are discarded. Meninges are completely removed and a single cut is made to separate the cortex and hippocampus from remaining structures. The cortex and hippocampus are minced into pieces approximately one mm on edge, incubated in 0.25 % trypsin for 20 minutes at 37° C., and dissociated into a single cell suspension by repeated passage through a flame-polished pipette. The suspension is plated at 3×105 cells per 60 mm plate in DMEM-complete. The following day, debris is washed from the plates and the adherent cells are then grown in DMEM supplemented with 10% horse serum (DMEM/HS) for 7–10 days. At this time, the glial cells have overgrown any neurons and the plates are approximately 85 % confluent. Six hours prior to the neuronal dissection, the glial monolayers are rinsed with Hanks balanced salt solution and the medium replaced with N2.1 medium (DMEM supplemented with 20 nM progesterone, 100 µM putrescine, 30 nM selenium dioxide, 5 µg/ml insulin, 100 µg/ml transferrin, 55 µg/ml sodium pyruvate, 750 µg/ml ovalbumin and 2 mM glutamine) containing 2% FBS, to allow the glia to condition this medium with diffusible factors necessary for survival of the primary septal or hippocampal neurons.

The neuronal cultures are established following essentially the above protocol. The septal and hippocampal regions are dissected from rat embryos of E16 and E17, respectively. The septa or hippocampi are pooled and dissociated into a single cell suspension as above except trypsinization is for 15 minutes. $2 \times 10^4$ cells are plated per 15 mm glass coverslip in DMEM/HS. Each coverslip has been coated with polylysine (0.5 mg/ml) and equipped, at the periphery, with 3 small paraplast feet less than 1 mm high. After 4 hours, the coverslips are inverted over the glial plane, with seven coverslips per 60 mm glial plate. The neurons and glia face each other and share medium, but are not in direct contact. On day 3 of coculture, the glial layer is nearly confluent and an antimitotic (cytosine arabinoside or fluro-deoxyuridine) is added. The antimitotic prevents the proliferation of glial cells on the coverslip cultures as well as the development of neuronal populations that are not post-mitotic. For fusions, the bilaminar culture system is inverted so that the neurons are on the surface of the plate (about $5 \times 10^5$/35 mm dish) and the glia are on plastic coverslips.

Neurons in this system survive for periods exceeding one month and develop appropriate morphological, neurochemical, and excitable properties. The neurons grown on coverslips are amenable to immunocytochemical, neurochemical, and electrophysiological analyses. The proportions of cholinergic, GABAergic, and LNGFR positive neurons have been identified in E16 septal bilaminar cultures with cholinergic neurons comprising up to 5 % of the neuronal population. Although 5 % ChAT-positive cells is sufficient to ensure generation of cholinergic hybrid cells, it is desirable to utilize primary cultures in which the proportion of cholinergic neurons is maximal.

Immunocytochemical characterization is performed by fixing the cells in 3 % paraformaldehyde/0.1% glutaraldehyde for 5 minutes. Cells are counted in a strip bisecting each coverslip, the width of the strip defined by the field of view through the 40× objective. We have previously determined the statistical validity of this sampling procedure. These counts include both stained and unstained cells to compute relative cell proportions and survival. This procedure is performed on both untreated cultures and parallel cultures exposed to 100 µg/ml NGF; although NGF has no apparent effect on E16 neurons it may have an effect on the younger, E14, neurons. Based on these numbers and those already obtained from E16 cultures, we use the cultures in which optimal proportions of ChAT-, GABA- and NGFR-positive neurons are present, for cell fusion.

An alternative approach to obtain septal cultures enriched for cells bearing a particular neurotrophin receptor, is to kill septal neurons by removing them from the glial cell layer and rescue a subpopulation of responsive neurons by addition of a known neurotrophin or cocktail of known neurotrophins. The utility of this approach is indicated by preliminary results in which a subpopulation of septal neurons was rescued by addition of NGF or NGF+ bFGF to glial conditioned medium.

Fully differentiated primary cultures (21 days) are used for fusions with the object of "fixing" the most differentiated characteristics. If these fail to form viable hybrids, a condition which might be evidenced by the formation of heterokaryons but not mononucleate fusion products, progressively younger primary cultures are used. For the fusion, exponentially growing transductant HPRT– cells are harvested by trypsinization, and plated on the primary neuronal monolayers. The plating densities of the primary cultures and the ratio of immortal to primary cells can be adjusted to optimize hybrid formation. The next day the transductant primary cultures are washed gently with SCFM. The medium is removed, and 1.5 ml/35 mm plate of 50% polyethylene glycol 1000 (PEG) is applied. After 1 minute, or less if toxicity is too great, the PEG is rapidly but gently aspirated and the plates rinsed three times with SCFM. 10% FBS is added and the cells incubated overnight.

Two days later the fusion products are harvested and plated into HAT-G418 medium. HAT kills unfused transductant cells and those hybrids which do not retain an HPRT+ allele. The G418 kills unfused primary cells. The resultant hybrids are maintained by replacing half of the medium every week. In some septal and hippocampal dishes, selection takes place in the presence of a cocktail of neurotrophins in case they are required to maintain neuronal subpopulations. Some of the hippocampal fusion plates are set up in a way as to optimize the probability of obtaining hybrids expressing the NMDA subtype of glutamate receptor. To increase the likelihood of obtaining a NMDA receptor expressing line, some fusion plates contain glutamate receptor blocking agents such as AP-5 and DVQX. The rationale for this procedure is the fact that PEG treatment and cell fusion result in substantial cell death which can raise the levels of extracellular K+, thus eliciting cellular depolarization and the release of excitotoxic substances which may eliminate cells expressing the glutamate receptor.

Genetic differences between the strains selected for the transductant parent and the primary parent permit verification of the hybrid nature of their fusion products. The capacity of the lines to express isozymes (e.g., glo-1, pep-3, pgd, or esterases) characteristic of each parent (Bender, et al. 1984; Hedrich 1990) are examined. Protein samples from the hybrid lines are separated by starch gel electrophoresis and incubated with a substrate specific for these enzymes (Siciliano, et al. 1987; Eves, et al. 1981). The two parental isozymes have differing electrophoretic mobilities and appear as distinct bands in the presence of a chromogen. Lines which express isozymes from both parents are considered hybrid in nature. Hybrids are expected to have a near tetraploid complement of chromosomes.

To insure that the hybrid lines can be manipulated like their transductant parent, the morphological and growth properties of the hybrids are examined at 33° C. and 39° C. as detailed above. Cytoskeletal, neurotransmitter, and excitable properties are analyzed as described above for transductant lines.

The present invention contemplates a process of screening substances for their ability to interact with a neuronal cell from a specific brain region comprising the steps of providing a hybrid neuronal cell of the present invention, and testing the ability of selected substances to interact with that cell.

Utilizing the methods and compositions of the present invention, screening assays for the testing of candidate substances such as drugs can be derived. A candidate substance is a substance which potentially can interact with or modulate, a neuronal cell. A method of the present invention makes it possible to produce large quantities of neuronal cells for use in screening assays.

A screening assay of the present invention generally involves determining the ability of a candidate substance to affect the function of the neuronal cell. Typically, a method includes preparing hybrid neuronal cell in accordance with the procedure set forth hereinbefore, followed by testing the cell with a candidate substance to determine the ability of the substance to affect the physiological function of the cell.

As is well known in the art, a screening assay cell under biological conditions suitable for cell viability. These conditions include but are not limited to pH, temperature, tonicity, and the like. pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. Other biological conditions needed for cell viability are well known in the art.

The foregoing preferred embodiments are illustrative of the present invention and are not limiting of the specification and claims in any way.

REFERENCES

The following references, as well as all references recited in this patent, are incorporated herein by reference.

1. Alt, F., Blackwell, K., and Yancopoulos, G. D. (1987). *Science*, 238, 1079.
2. Ausubel, F. M., Brent, R., Kingston, R. E., et al (1989) *Current protocols in molecular biology*, Greene Publishing Associates, and John Wiley and Sons: N.Y.
3. Banker, G. and Goslin, K. (1991). *In Culturing nerve cells* (ed. G. Banker and K. Goslin), pp. 11–39. MIT Press, Cambridge, Mass.
4. Banker, G. A. and Cowan, W. M. (1979) *J. Comp. Neurol.* 187: 469–494.
5. Bayer, S. A. (1980) *J. Comp. Neurol.* 190: 89–106.
6. Bayer, S. A. (1979). *J. Comp. Neurol.*, 183, 89–106.
7. Bay, C., Dickerson, M. R., Davis, R. E. and Spiegel, K. (1990) *Soc. Neurosci. Abs.* 16: 992.
8. Binder, L., Frankfurter, A. & Rebhun, L. (1986) *Ann. N.Y. Acad. Sci.* 466, 145–166.
9. Birren, S. J. and Anderson, D. J. (1990) *Neuron* 4: 189–201.
10. Bottenstein, J. E. (1981). *In Functionally differentiated cell lines* (ed. G. Sato), pp. 155–84. Alan R. Liss, New York.

11. Bradford, M. M. (1976) *Analytical Biochemistry* 72: 248–254.
12. Caceres, A. and Kosik, K. S. (1990) *Nature* 343: 461–463.
13. Cattaneo, E. and McKay, R. (1990) *Nature* 347: 762–765.
14. Cepko, C. L. (1989). *Ann. Rev. Neurosci.*, 12, 47.
15. Chandler, C. E., Parsons, L. M., Hosang, M. & Shooter, E. M., (1984) *J. Biol. Chem.* 259, 6882–6889.
16. Chomczynski, P. (1987) *Biochemistry* 162: 156–159.
17. Cordon-Cardo, C., Tapley, P., Jing, S., et al (1991) *Cell* 66: 173–183.
18. Cotman, C. W. and Iversen, L. L. (1987) *TINS* 10: 263–265.
19. Cotman, C. W., Monaghan, D. T., Ottersen, O. P. and Storm-Mathisen, J. (1987) *TINS,* 10: 273–280.
20. Dreyfus, C. F., Bernd, P., Martinez, H. J., Rubin, S. J. and Black, I. B. (1989) *Exp. Neurol.* 104: 181–185.
21. Eves, E. M., Kwon, J., and Wainer, B. H. (1991). *Soc. Neurosci. Abs.,* 17, 37.
22. Eves, E. M. and Farber, R. A. (1981) *Proc. Natl. Acad. Sci.* (U.S.A.) 78: 1768–1772.
23. Eves, E. M. and Farber, R. A. (1983) *Som. Cell Genet.* 9: 771–778.
24. Eves, E. M., Lee, H. J., Tucker, M. S., Rosner, M. R., and Wainer, B. H. (1990). *Soc. Neurosci. Abs.,* 16, 1149.
25. Favaron, M., Manev, H., Alho, H., et al (1988) *Proc. Natl. Acad. Sci.* (U.S.A.) 85: 7351–7355.
26. Fonnum, F. (1975) *J. Neurochem.* 24: 407–409.
27. Frederiksen, K., Jat, P. S., Valtz, N., Levy, D. and McKay, R. (1988) *Neuron* 1: 439–448.
28. Freund, T. F. and Antal, M. (1988). *Nature,* 336, 170–173.
29. Giotta, G. S., Heltzmann, J. and Cohn, M. (1980) *Brain Res.* 202: 445–458.
30. Goslin, K. and Banker, G. (1991) *Culturing Nerve Cells* (edited by Banker, G. and Goslin, K.), MIT Press: Cambridge, Mass., p. 251–281.
31. Goslin, K., Schreyer, D. J., Skene, J. H. and Banker, G. (1988) *Nature* 336: 672–674.
32. Gottlieb, D. I., Chang, Y. C. and Schwob, J. E. (1988) *Proc. Natl. Acad. Sci.* (U.S.A.) 83: 8808–8812.
33. Greene, L. A., Sobeih, M. M., and Teng, K. K. (1991) *Culturing nerve cells* (ed. G. Banker and K. Goslin), pp. 207–26. MIT Press, Cambridge, Mass.
34. Greene, L. A., Shain, W., Chalazonitis, A., et al. (1975). *Proc. Natl. Acad. Sci. USA,* 72, 4923.
35. Hammond, D. N., Lee, H. J., Tonsgard, J. H., and Wainer, B. H. (1990). *Brain Res.,* 512, 190–200.
36. Hammond, D. N., Wainer, B. H., Tonsgard, J. H., and Heller, A. (1986). *Science,* 234, 1237–1240.
37. Hartikka, J. and Heft, F. (1988)*J. Neurosci.* 8: 2967–2985.
38. Hartikka, J. and Heft, F. (1988)*J. Neurosci. Res.* 21: 352–364.
39. Haskell, B. E., Stach, R. W. and Werrbach-Perez, K. (1987) *Cell and Tissue Research* 247: 67–73.
40. Hsie, A. W., Brimer, P. A., Mitchell, T. J. and Gosslee, D. G. (1975) *Som. Cell Genet.* 1: 247–261.
41. Jat, P. S. and Sharp, P. A. (1989) *Mol. Cell. Biol.* 9: 1672–1681.
42. Kamegai, M., Niijima, K., Kunishita, T., et al. (1990). *Neuron,* 4, 429–436.
43. Kamegai, M., Konishi, Y., and Tabira, T. (1990). *Brain Res.,* 532, 323.
44. Katsuki, M., Sato, M., Kimura, M., Yokoyama, M. and Nomura, T. (1988) *Science* 241: 593–595.
45. Klein, R., Nanduri, V., Jing, S., et al (1991) *Cell* 66: 395–403.
46. Klein, R., Parada, L. F., Coulier, F. and Barbacid, M. (1989) *The EMBO Journal* 8: 3701–3709.
47. Kohler, G. and Milstein, C. (1975). *Nature,* 256, 495.
48. Kontur, P., Dawson, R. and Monjan, A. (1984) *J. Neurosci. Meth.* 11: 5–18.
49. Lamballe, F., Klein, R. and Barbacid, M. (1991) *Cell* 66: 967–979.
50. Large, T. H., Bodary, S. C., Clegg, D. O., Weskamp, G., Otten, U. and Reichardt, L. F.(1986) *Science* 234: 352–355.
51. Lee, H. J., Hammond, D. N., Large, T. H., and Wainer, B. H. (1990). *Devel. Brain Res.,* 52, 219–228.
52. Lee, H. J., Hammond, D. N., Large, T. H., et al. (1990). *J. Neurosci.,* 10, 1779.
53. Lee, H. J., Hammond, D. N., Large, T. H., et al (1990) *J. Neurosci.* 10: 1779–1787.
54. Lee, F., Mulligan, R., Berg, P. and Ringold, G. (1981) *Nature* 294: 228–232.
55. Lee, V. M.-Y., Page, C. D., Wu, H. -L. and Schlaepfer, W. W. (1984) *J. Neurochem.* 42: 25–32.
56. Lee, V. M.-Y., Carden, M. J., Schlaepfer, W. W. and Trojanowski, J. Q. (1987) *J. Neurosci.* 7: 3474–3488.
57. Lendahl, U. and McKay, R. D. G. (1990). *Trends Neurosci.,* 13, 132.
58. Levey, A. I., Armstrong, D. M., Atweh, S. F., Terry, R. D. and Wainer, B. H. (1983) *J Neurosci.* 3: 1–9.
59. Littlefield, J. W. (1966) *Exp. Cell Res.* 41: 190–196.
60. Maisonpierre, P. C., LeBeau, M. M., Espinosa III, R., Ip, N.Y., Belluscio, L., De la Monte, S. M., Squinto, S., Furth, M. E. & Yancopoulos, G. D. (1991) *Genomics,* 10, 558–568.
61. Martin-Zanca, D., Barbacid, M. and Parada, L. F. (1990) *Genes and Development* 4: 683–694.
62. Maniatis, T., Fritsch, E. F. and Sambrook, J. (1987) Molecular Cloning—a laboratory manual. Cold Spring Harbor Laboratory: Cold Spring Harbor, N.Y.
63. Morimoto, B. H. and Koshland, D. E.,Jr. (1990) *Proc. Natl. Acad. Sci.*(U.S.A.) 87: 3518–3521.
64. Mulligan, R. C. and Berg, P. (1981) *Proc. Natl. Acad. Sci.* (U.S.A.) 78: 2072–2076.
65. O'Neill, J. P., Brimer, P. A., Machanoff, R., Hirsch, J. P. and Hsie, A. W. (1977) *Mutation Res.* 45:91–10 1.
66. Paige, C. J. and Wu, G. E. (1989). *FASEB J.,* 3, 1818.
67. Platika, D., Boulos, M. H., Baizer, L., and Fishman, M. C. (1985). *Proc. Natl. Acad. Sci. USA,* 82, 3499.
68. Purves, D. (1988). *Body and brain: a trophic theory of neural connections.* Harvard University Press, Cambridge, Mass.
69. Renfranz, P. J., Cunningham, M. G. and McKay, R. D. G. (1991) *Cell* 66: 713–729.
70. Richardson, U. I., Liscovitch, M. and Blusztajn, J. K. (1989) *Brain Res.* 476:323–331.
71. Roback, J. D., Large, T. H., Otten, U. and Wainer, B. H. (1990) *Dev. Biol.* 137:451–455.
72. Rodriquez-Tebar, A. and Rohrer, H. (1991) *Development* 112: 813–820.
73. Ronnett, G. V., Hester, L. D., Nye, J. S., Connors, K., and Snyder, S. H. (1990). *Science,* 248, 603.
74. Sambrook, J., Fritsch, E. F. and Maniatis, T. (1989) Molecular cloning. A laboratory manual. Cold Spring Harbor Laboratory Press: Cold Spring Harbor, N.Y.
75. Scholz, W. K. & Palfrey, H. C. (1991) *J. Neurosci.* 11, 2422–2432.
76. Schubert, D. (1984). *In Developmental biology of cultured nerve, muscle, and glia* (ed. D. Schubert), pp. 1–25. John Wiley, New York.

77. Semba, K. and Fibiger, H. C. (1988). *J. Comp. Neurol.*, 269, 87.
78. Shalaby, I. A., Won, L. and Wainer, B. (1987) Brain Res. 402: 68–77.
79. Shaw, E. I. and Hsie, A. W. (1978) *Mutation Res.* 51: 237–254.
80. Shay, J. W. (1982). *Techniques in somatic cell genetics.* Plenum Press, New York.
81. Siciliano, M. J. and White, B. F. (1987). *Methods in enzymology* (ed.), Vol. 151, pp. 169–194. Academic Press, Orlando, Fla.
82. Springer, J. E., Koh, S., Tayrien, M. W. and Loy, R. (1987) *J. Neurosci. Res.* 17: 111–118.
83. Tishler, A. S. and Greene, L. A. (1975). *Nature,* 258, 341–342.
84. Trojanowski, J. Q., Kelsten, M. L. & Lee, V. M.-Y. (1989) *Am. J. Pathol.* 135, 747–758.
85. Tucker, R. P., Binder, L. I. and Matus, A. I. (1988) *J. Comp. Neurol.* 271: 44–55.
86. Tucker, M. S., Eves, E. M., Hou, X. Y., Wainer, B. H., and Rosner, M. R. (1990). *E Soc. Neurosci. Abs.,* 16, 1149.
87. Tucker, M. S., Eves, E. M., Hou, X. Y., Wainer, B. H., and Rosner, M. R. (1991). *FASEB J.,* 5, A1622.
88. Wainer, B. H., Levey, A. I., Rye, D. B., Mesulam, M.-M., and Mufson, E. J. (1985). *Neurosci. Lett.,* 54, 45–52.
89. Weskamp, G. and Otten, U. (1987) *J. Neurochem.* 48: 1779–1786.
90. Zon, G. (1988) *Pharmaceutical Research* 5: 539–549.

What is claimed is:

1. A process of preparing a hybrid neuronal cell from a specific brain region, said process comprising the steps of:
   a) transducing a primary embryonic brain cell from said brain region with a temperature-sensitive oncogene to produce a transductant cell; and
   b) fusing said transductant cell with a mature primary neuron from said brain region to produce said hybrid cell.
2. The process according to claim 1 wherein said brain region is the septum or the hippocampus.
3. The process according to claim 1 wherein said temperature-sensitive oncogene is contained in a retrovirus.
4. The process according to claim 1 wherein said temperature-sensitive oncogene is a temperature-sensitive mutant of the SV40 large T antigen.
5. The process according to claim 1 further comprising the step of selecting for said transductant cell before the fusing step.
6. The process according to claim 5 wherein selecting is mutagenizing said transduced cell to eliminate the HPRT gene and produce a HPRT$^-$ cell, and culturing said HPRT$^-$ cell in HAT medium.
7. A hybrid neuronal cell produced by the process of claim 1.
8. A process of screening a substance for its ability to modulate a function of a neuronal cell from a specific brain region, said process comprising the steps of:
   a) providing a hybrid neuronal cell prepared in accordance with the process of claim 1 from said specific brain region; and
   b) testing the ability of said substance to modulate the function of said hybrid cell.

* * * * *